(12) United States Patent
Poinsard et al.

(10) Patent No.: US 10,202,346 B2
(45) Date of Patent: Feb. 12, 2019

(54) PHENOL DERIVATIVES AND THE PHARMACEUTICAL OR COSMETIC USE THEREOF

(71) Applicant: Galderma Research & Development, Biot (FR)

(72) Inventors: Cedric Poinsard, Le Plan de Grasse (FR); Pascal Collette, Le Cannet (FR); Pascale Mauvais, Antibes (FR); Jean-Michel Linget, Benfeld (FR); Sandrine Rethore, Valbonne (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 14/809,815

(22) Filed: Jul. 27, 2015

(65) Prior Publication Data

US 2016/0068488 A1 Mar. 10, 2016

Related U.S. Application Data

(63) Continuation of application No. 13/519,120, filed as application No. PCT/FR2010/052874 on Dec. 22, 2010.

(60) Provisional application No. 61/282,151, filed on Dec. 23, 2009.

(30) Foreign Application Priority Data

Dec. 23, 2009 (FR) ..................... 09 59477

(51) Int. Cl.
C07D 213/74 (2006.01)
(52) U.S. Cl.
CPC ................. *C07D 213/74* (2013.01)
(58) Field of Classification Search
None
See application file for complete search history.

(56) References Cited

U.S. PATENT DOCUMENTS

| 4,578,390 | A | 3/1986 | Jensen et al. |
| 7,064,124 | B2 | 6/2006 | Suzuki et al. |
| 2007/0017040 | A1 | 1/2007 | Pasquier et al. |
| 2009/0196912 | A1 | 8/2009 | Eickhoff et al. |

FOREIGN PATENT DOCUMENTS

| AU | 39876/93 B2 | 1/1994 |
| DE | 202 17 957 U1 | 3/2003 |
| EP | 0 580 459 A1 | 1/1994 |
| WO | 2005/042464 A1 | 5/2005 |
| WO | 2006/010637 A2 | 2/2006 |

OTHER PUBLICATIONS

Freshney, RI. Culture of Animal Cells: A Manual of Basic Technique. John Wiley and Sons. 2005, 5th Ed., p. 8.*
National Research Council (US) Steering Committee on Identification of Toxic and Potentially Toxic Chemicals for Consideration by the National Toxicology Program. Toxicity Testing: Strategies to Determine Needs and Priorities. Washington (DC): National Academies Press (US); 1984.*
Paris et al., "Phenylphenols, biphenols, bisphenol-A and 4-tert-octylphenol exhibit α and β estrogen activities and antiandrogen activity in reporter cell lines," Molecular and Cellular Endocrinology, 2002, pp. 43-49, vol. 193.
Pathak et al., "Antiandrogenic Phenolic Constituents From Dalbergia Cochinchinensis," Phytochemistry, 1997, pp. 1219-1223, vol. 46, No. 7.
Schiller et al., "3-(Cyclohexenonyl)-4-(4-hydroxyphenyl)hex anes: antiandrogens derived from the estrogen hexestrol," Arch. Pharm. 1990, pp. 417-420, vol. 323.
English language translation of the Written Opinion of the International Searching Authority (PCT/ISA/237) dated Aug. 7, 2012, in corresponding International Patent Application No. PCT/FR2010/052874.
Shang, "The anion recognition properties of Schiff base or its reductive system based on 2,2'-bipyridine derivatives," Spectrochimica Acta Part A, Jun. 2009, pp. 1117-1121, vol. 72.
Carey, FA. Organic Chemistry 6th Ed. McGraw Hill. 2006, Chapter 1, pp. 9-10.

* cited by examiner

*Primary Examiner* — Heidi Reese
(74) *Attorney, Agent, or Firm* — Sunit Talapatra; Foley & Lardner LLP

(57) ABSTRACT

The use of compounds in the treatment of skin disorders is described. In particular, use of a compound of formula (I):

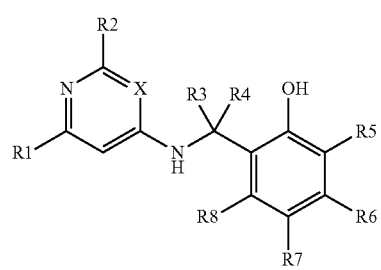

or one of its pharmaceutically acceptable salts, solvates or hydrates in the preparation of a medicament to treat skin pathologies is described.

10 Claims, No Drawings

PHENOL DERIVATIVES AND THE PHARMACEUTICAL OR COSMETIC USE THEREOF

CROSS-REFERENCE TO PRIOR APPLICATIONS

This application is a continuation of U.S. patent application Ser. No. 13/519,120, filed Oct. 3, 2012, which is a National Stage of PCT/FR2010/052874, filed Dec. 22, 2010, and designating the United States (published in French on Jun. 30, 2011, as WO 2011/077046 A1; the title and abstract were published in English), which claims priority of FR 0959477, filed Dec. 23, 2009, and U.S. Provisional Application No. 61/282,151, filed Dec. 23, 2009, each hereby incorporated by reference in its entirety and each assigned to the assignee hereof.

The present invention relates to novel compounds of general formula:

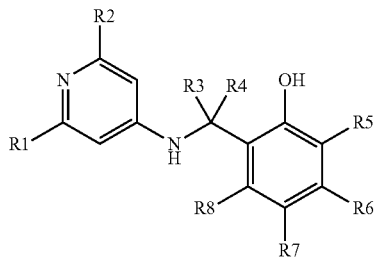

and to the cosmetic or pharmaceutical use thereof.

The present invention proposes to provide novel phenolic derivatives which are powerful androgen receptor modulators.

Among the prior art documents describing molecules which modulate androgen receptor activity, mention may, for example, be made of the phenylimidazolines described in patent application EP580459, or application WO 200542464.

The invention relates to novel phenolic derivatives that correspond to general formula (I) below:

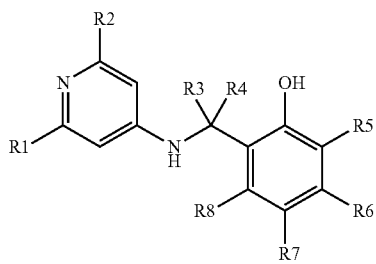

in which:

$R_1$ represents a $C_{1-6}$ alkyl, $C_{3-7}$ cycloalkyl, $C_{1-6}$ alkyloxy, —S(O)$_m$—$C_{1-6}$ alkyl, $C_{1-6}$ fluoroalkyl, $C_{1-6}$ flouroalkyloxy, —(CH$_2$)$_n$—$C_{3-9}$ cycloalkyl, —(CH$_2$)$_n$—$C_{3-9}$ cycloalkyl, $C_{2-6}$ alkyl-OH, —(CH$_2$)$_n$—$C_{1-6}$ alkyloxy, —(CH$_2$)$_n$—$C_{1-6}$ fluoroalkyl, —(CH$_2$)$_p$—O—$C_{1-6}$ fluoroalkyl, COR$_a$, CN, NO$_2$ or NR$_9$R$_{10}$ group, a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different $R_b$ groups;

$R_2$ represents a $C_{1-6}$ alkyl, $C_{3-7}$ cycloalkyl, $C_{1-6}$ alkyloxy, —S(O)$_f$—$C_{1-6}$ alkyl, $C_{1-6}$ fluoroalkyl, $C_{1-6}$ fluoroalkyloxy, —(CH$_2$)$_f$—$C_{3-9}$ cycloalkyl, —(CH$_2$)$_f$—$C_{3-9}$ cycloalkyl, $C_{2-6}$ alkyl-OH, —(CH$_2$)$_f$—$C_{1-6}$ alkyloxy, —(CH$_2$)$_f$—$C_{1-6}$ fluoroalkyl, —(CH$_2$)$_q$—O—$C_{1-6}$ fluoroalkyl, COR$_d$, CN, NO$_2$ or NR$_9'$R$_{10'}$ group, a hydrogen, a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different $R_b$ groups;

$R_3$ and $R_4$ are identical or different and represent a hydrogen atom or a $C_{1-9}$ alkyl, $C_{3-9}$ cycloalkyl, $C_{1-6}$ fluoroalkyl, —(CH$_2$)$_x$—$C_{3-9}$ cycloalkyl, —$C_{2-6}$ alkyl-OH, —(CH$_2$)$_p$—$C_{1-6}$ alkyloxy, —(CH$_2$)$_k$—$C_{3-7}$ cycloalkyl, —(CH$_2$)$_k$—$C_{1-6}$ fluoroalkyl or —(CH$_2$)$_r$—O—$C_{1-6}$ fluoroalkyl group.

Optionally, the $R_3$ and $R_4$ groups can form, with the carbon atom which bears them, a $C_{3-9}$ cycloalkyl group or a heterocycle such as tetrahydrofuran, tetrahydropyran, tetrahydrothiopyran, tetrahydro-1-oxythiopyran or tetrahydro-1,1-dioxythiopyran;

$R_5$, $R_6$, $R_7$ and $R_8$ are identical or different and represent either a hydrogen atom or a $C_{1-6}$ alkyl, $C_{3-7}$ cycloalkyl, $C_{1-6}$ alkyloxy, —S(O)$_g$—$C_{1-6}$ alkyl, $C_{1-6}$ fluoroalkyl, $C_{1-6}$ fluoroalkyloxy, —(CH$_2$)$_j$—$C_{3-9}$ cycloalkyl, —(CH$_2$)$_j$—$C_{3-9}$ cycloalkyl, —$C_{1-6}$ alkyl-OH, —(CH$_2$)$_j$—$C_{1-6}$ alkyloxy, —(CH$_2$)$_j$—$C_{1-6}$ fluoroalkyl, —(CH$_2$)$_s$—O—$C_{1-6}$ fluoroalkyl, COR$_e$, CN or NR$_{11}$R$_{12}$ group, or a halogen or a phenyl or heteroaryl group containing either a) from 1 to 4 nitrogen atoms or b) an oxygen or sulphur atom and 1 or 2 nitrogen atom(s).

These phenyl and heteroaryl groups may be optionally substituted with one to three identical or different $R_c$ groups;

$R_a$, $R_d$ and $R_e$ are identical or different and represent a $C_{1-6}$ alkyl, $C_{1-6}$ alkyloxy or NR$_{13}$R$_{14}$ group;

$R_b$ and $R_c$ are identical or different and represent a halogen, or a $C_{1-6}$ alkyl, $C_{3-7}$ cycloalkyl, $C_{1-6}$ alkyloxy, —S(O)$_u$—$C_{1-6}$ alkyl, $C_{1-6}$ fluoroalkyl, $C_{1-6}$ fluoroalkyloxy, —(CH$_2$)$_t$—$C_{3-7}$ cycloalkyl, —(CH$_2$)$_i$—$C_{3-7}$ cycloalkyl, $C_{1-6}$ alkyl-OH, —(CH$_2$)$_i$—$C_{1-6}$ alkyloxy, —(CH$_2$)$_i$—$C_{1-6}$ fluoroalkyl, —(CH$_2$)$_t$—O—$C_{1-6}$ fluoroalkyl, COR$_a$, CN, or NR$_{15}$R$_{16}$ group;

$R_9$, $R_{9'}$, $R_{10}$, $R_{10'}$, $R_{11}$, $R_{12}$, $R_{13}$, $R_{14}$, $R_{15}$ and $R_{16}$ are identical or different and represent a hydrogen atom, or a $C_{1-6}$ alkyl, $C_{3-7}$ cycloalkyl, —(CH$_2$)$_h$—$C_{3-7}$ cycloalkyl —(CH$_2$)$_h$—$C_{1-6}$ fluoroalkyl group.

Optionally, the $R_9$ and $R_{10}$ groups can form, with the nitrogen atom which bears them, a heterocycle such as azetidine, pyrrolidine, piperidine, azepane, morpholine or piperazine. Optionally, the $R_{9'}$ and $R_{10'}$ groups can form, with the nitrogen atom which bears them, a heterocycle such as: azetidine, pyrrolidine, piperidine, azepane, morpholine or piperazine. Optionally, the $R_{11}$ and $R_{12}$ groups can form, with the nitrogen atom which bears them, a heterocycle such as: azetidine, pyrrolidine, piperidine, azepane, morpholine or piperazine. Optionally, the $R_{13}$ and $R_{14}$ groups can form, with the nitrogen atom which bears them, a heterocycle such as: azetidine, pyrrolidine, piperidine, azepane, morpholine or piperazine. Optionally, the $R_{15}$ and $R_{16}$ groups can form, with the nitrogen atom which bears them, a heterocycle such as: azetidine, pyrrolidine, piperidine, azepane, morpholine or piperazine:

h, i, j, k, l and n are different or identical and are equal to 1, 2 or 3;

f, g, m and u are different or identical and are equal to 0, 1 or 2;

p, q, r, s and t are different or identical and are equal to 2, 3 or 4;

and also the pharmaceutically acceptable salts, solvates or hydrates thereof and the conformers or rotamers thereof.

The compounds of formula (I) may comprise one or more asymmetric carbon atoms. They may thus exist in the form of a mixture of enantiomers or of diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts are advantageously prepared with pharmaceutically acceptable acids, but the salts of other acids that are useful, for example, for purifying or isolating the compounds of formula (I), also form part of the invention. These acids may be, for example, picric acid, oxalic acid or an optically active acid, for example a tartaric acid, a dibenzoyltartaric acid, a mandelic acid or a camphorsulphonic acid, and those that form physiologically acceptable salts, such as hydrochloride, hydrobromide, sulphate, hydrogen sulphate, dihydrogen phosphate, maleate, fumarate, 2-naphthalenesulphonate or para-toluenesulphonate. For a review of physiologically acceptable salts, see the Handbook of Pharmaceutical Salts: Properties, Selection and Use by Stahl and Wermuth (Wiley-VCH, 2002).

The solvates or hydrates may be obtained directly after the synthesis process, compound (I) being isolated in the form of a hydrate, for example a monohydrate or hemihydrate, or of a solvate of the reaction or purification solvent.

In the context of the invention, the following definitions apply:

$C_{b-c}$ in which b and c may take values from 1 to 9: a carbon-based chain of b to c carbon atoms, for example $C_{1-6}$ is a carbon-based chain that may contain from 1 to 6 carbon atoms, alkyl: a linear or branched saturated aliphatic group, for example a $C_{1-6}$ alkyl group represents a linear or branched carbon-based chain of 1 to 6 carbon atoms, for example a methyl, ethyl, propyl, isopropyl, butyl, isobutyl, tert-butyl, pentyl or hexyl, cycloalkyl: a cyclic, optionally branched, saturated carbon-based chain containing from 3 to 7 carbon atoms. By way of example, a $C_{3-7}$ cycloalkyl group represents a carbon-based chain containing from 3 to 7 carbon atoms, for example a cyclopropyl, cyclobutyl, cyclopentyl, cyclohexyl or cycloheptyl, heterocycle: a cyclic or bicyclic, saturated or unsaturated hydrocarbon-based chain comprising one or more heteroatoms chosen from O, S and N, heteroaryl: an aromatic heterocycle, for example a pyridinyl, pyrazinyl, pyrimidinyl, pyridazinyl, triazinyl, pyrazolyl, isooxazolyl, oxadiazolyl, thiazolyl, thiadiazolyl, triazolyl or imidazolyl group, halogen: a fluorine, chlorine or bromine atom, alkyloxy: an —O-alkyl group, alkylthio: an —S-alkyl group, fluoroalkyl: an alkyl group in which one or more hydrogen atoms have been replaced with a fluorine atom, fluoroalkyloxy: an alkyloxy group in which one or more hydrogen atoms have been replaced with a fluorine atom:

The group (A) of the compounds of formula (I) defined above is preferred, in which compounds:

$R_1$ represents a halogen, or a methyl, ethyl, isopropyl, trifluoromethyl, nitrile, nitro, methoxy, ethoxy, isopropoxy, thiomethyl, thioethyl, thioisopropyl group, $R_2$ represents a hydrogen atom, a halogen, or a methyl, ethyl, isopropyl, trifluoromethyl, nitrile, nitro, methoxy, ethoxy, isopropoxy, thiomethyl, thioethyl or thioisopropyl group, and more particularly when:

$R_1$ represents a halogen, or a methyl, ethyl, methoxy, ethoxy, thiomethyl, thioethyl or trifluoromethyl group, $R_2$ represents a hydrogen atom, a halogen, or a methoxy, ethoxy, thiomethyl, thioethyl or trifluoromethyl group.

The compounds below, and the pharmaceutically acceptable salts, solvates and hydrates thereof and the conformers or rotamers thereof, are particularly preferred:

2-[(2-Bromo-6-methoxypyridin-4-ylamino)methyl]phenol

2-[(2-Chloropyridin-4-ylamino)methyl]phenol

2-[(2-Bromopyridin-4-ylamino)methyl]phenol

2-[(2-Bromopyridin-4-ylamino)methyl]-4-fluorophenol

2-[(2-Methoxypyridin-4-ylamino)methyl]phenol

2-[(2-Trifluoromethyloyridin-4-ylamino)methyl]phenol

4-Fluoro-2-[(2-methoxypyridin-4-ylamino)methyl]phenol

2-[(2-Bromo-6-methoxypyridin-4-ylamino)methyl]-4-fluorophenol

2-[(2-Bromo-6-methoxypyridin-4-ylamino)methyl]-6-fluorophenol

2-[(2-Bromo-6-methoxypyridin-4-ylamino)methyl]-6-methylphenol

2-[(2-Bromo-6-methoxypyridin-4-ylamino)methyl]-5-fluorophenol

2-[(2-Bromo-6-methoxypyridin-4-ylamino)methyl]-3-flourophenol

2-[(2-Bromo-6-methoxypyridin-4-ylamino)methyl]-3-fluorophenyl

2-[(2-Chloro-6-methoxypyridin-4-ylamino)methyl]phenol

2-[(2-Bromo-6-methoxypyridin-4-ylamino)methyl]-5-methylphenol

2-[(2-Chloro-6-methoxypyridin-4-ylamino)methyl]-4-fluorophenol

2-[(2-Bromo-6-methylpyridin-4-ylamino)methyl]phenol

2-[(2-Bromo-6-methylpyridin-4-ylamino)methyl]-4-fluorophenol

2-[1-(2-Bromo-6-methoxypyridin-4-ylamino)ethyl]phenol

2-[1-(2-Bromo-6-methoxypyridin-4-ylamino)propyl]-phenol

2-[(2-Bromo-6-ethoxypyridin-4-ylamino)methyl]phenol

2-[1-(2-Bromo-6-methoxypyridin4-ylamino)-1-methylethyl]phenol

2-[(2-Bromo-6-methylpyridin-4-ylamino)methyl]-5-fluorophenol

A subject of the invention is also a process for preparing the compounds of general formula (I).

In accordance with the invention, the compounds of formula (I) may be prepared by means of one of the three methods described in Scheme 1 below.

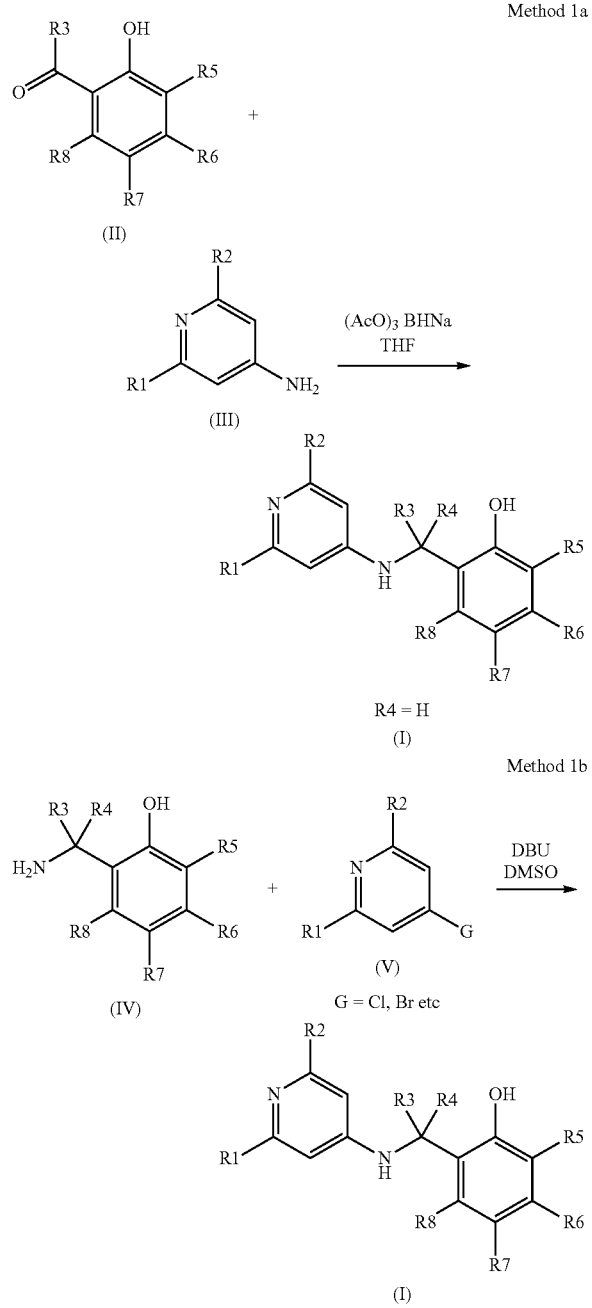

Scheme 1

The phenol compounds of formula (I) in which $R_1$, $R_2$, $R_3$, $R_4$, $R_5$, $R_6$, $R_7$ and $R_8$ are as defined above can be prepared by means of a reductive amination reaction between an aldehyde or a benzyl ketone (II) and an amine (III) in the presence of a reducing agent, such as, for example, and in a non-limiting manner, sodium triacetoxyborohydride, according to Method 1a illustrated in Scheme 1 and by analogy, for example, with the reactions described in *Org. Pro R. & D.* (2006) 971-1031.

The phenol compounds of formula (I) can be prepared by reaction between heterocycles (V) comprising a leaving group and benzyl amines (IV) in the presence of a base such as, in a non-limiting manner, 1,8-diazabicyclo[5.4.0]undec-7-ene, for example in a solvent such as dimethyl sulphoxide as described by Method 1b of Scheme 1. The term "leaving group" denotes a group well known to those skilled in the art, such as, in a non-limiting manner, a halogen, a mesylate, a tosylate or a triflate.

The functional groups that may be present in the reaction intermediates used in the process may be protected, either permanently or temporarily, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley & Sons, 1991, and in "Protecting Groups", Kocienski P. J., 1994, Georg Thierne Verlag.

The products which are subjects of the present invention have advantageous pharmacological properties; it was in particular noted that they modulated androgen receptor activity.

Tests given in the experimental section illustrate this androgen receptor-modulating activity. The products which are subjects of the present invention exhibit partial or total antagonist or agonist activities. Because of this activity, the products of the invention can be used as medicaments in humans or animals.

These properties make the products of general formula (I) of the present invention usable as medicaments for treating hormone-dependent cancers such as prostate cancer or breast cancer, and also for combating benign prostatic hyperplasia, early puberty, virilization, polycystic ovary syndrome, Stein-Levanthal syndrome, loss of libido, or endometriosis. The compounds exhibiting partial or total agonist activity can in particular be used for treating afflictions such as loss of muscle mass (sarcopenia), muscle atrophy, impotence and male sterility, abnormal male differentiation (hermaphroditism), hypogonadism or osteoporosis. The products of general formula (I) of the invention also find their cosmetic use for body or hair hygiene.

The products of general formula (I) of the invention also find their use in the treatment of hirsutism, acne, seborrhoea, oily skin, androgenic alopecia or hyperpilosity, and they can be used for the production of a medicament for preventing and/or treating hirsutism, androgenic alopecia, hyperpilosity, atopic dermatitis, or sebaceous gland disorders such as hyperseborrhoea, acne, oily skin or seborrhoeic dermatitis. The products of formula (I) can therefore be used in dermatology: they can be used alone or in combination. They can be combined in particular with an antibiotic product, such as derivatives of azelaic acid, fusidic acid or erythromycin or with a retinoid derivative such as tretinoin for the treatment of acne, or with a 5a-reductase inhibitor such as (5alpha, 17beta)-N-1,1-dimethylethyl-3-oxo-4-aza-androst-1-ene-17-carboxamide (or Finesteride, Merck, 13th edition) or azelaic acid or an androgen receptor-blocking agent for the treatment of acne, alopecia or hirsutism, or with a product that stimulates hair growth, such as Minoxidil, for the treatment of alopecia.

A subject of the present invention is also, as medicaments, the compounds of formula (I) as described above, and also the pharmaceutically acceptable salts and pharmaceutically acceptable solvates and/or hydrates thereof.

Several examples of preparation of active compounds of formula (I) according to the invention, and results of the biological activity of such compounds, are given hereinbelow as illustrations and with no limiting nature.

PROCEDURES

Example 1

2-[(2-Bromo-6-methoxypyridin-4-ylamino)methyl]phenol

Synthesis According to Scheme 1, Method 1a 400 mg (1.97 mmol) of 2-bromo-6methoxypyridin-4-ylamine (starting materials 1) are added to a mixture of 363 mg (2.96 mmol, 1.5 eq) of 2-hydroxybenzaldehyde (starting materials 2) and 184 mg (2.96 mmol, 1.5 eq) of acetic acid in 10 mL of THF in the presence of molecular sieve. After 5 minutes at ambient temperature, 835 mg (3.94 mmol, 2 eq) of sodium triacetoxyborohydride are added and the mixture is left to stir for 2 H at ambient temperature. The reaction medium is diluted with 50 mL of ethyl acetate and then the mixture is washed with 50 mL of a saturated solution of ammonium chloride, followed by three times 50 mL of water. The organic phase is concentrated to dryness and the residue is purified by silica chromatography, elution being carried out with a mixture of heptane/ethyl acetate (7/3). 2-[(2-Bromo-6-methoxypyridin-4-ylamino)methyl]phenol is obtained in the form of a beige solid.

Melting point=137° C.

NMR 1H (DMSO) 3.69 (s, 3H); 4.17 (d, 2H, J=5.2 Hz); 5.81 (s, 1H); 6.45 (s, 1H) 6.75 (t, 1H, J=7.4 Hz); 6.82 (d, 1H, J=8 Hz); 7.07 (t, 1H, J=7.7 Hz); 7.12 (d, 1H, J=7.4 Hz); 7.17-7.19 (m, 1H); 9.64 (s, 1H).

Examples 2 to 14

Examples 2 to 14 are described in Table 1 below. The compounds are synthesized according to the procedure described above, replacing the starting materials 1 and 2 mentioned in Example 1 with the products mentioned in Table 1.

TABLE 1

| Example # | IUPAC name | Starting material 1 | Starting material 2 | Melting point (° C.) | 1H NMR-400 MHz (s = singlet, d = doublet, t = triplet, m = multiplet, q = quartet, J = coupling constant in Hz) |
|---|---|---|---|---|---|
| 2 | 2-[(2-Chloropyridin-4-ylamino)methyl]phenol | 4-Amino-2-chloropyridine | 2-Hydroxybenzaldehyde | 200 | (DMSO) 4.21 (d, 2H, J = 5.7 Hz); 6.51-6.52 (m, 2H); 6.75 (t, 1H, J = 7.4 Hz); 6.84 (d, 1H, J = 8.0 Hz); 7.01-7.14 (m, 2H); 7.28-7.30 (m, 1H); 7.78 (d, 1H, J = 5.8 Hz); 9.65 (s, 1H) |
| 3 | 2[(2-Bromopyridin-4-ylamino)methyl]phenol | 2-Bromopyridin-4-ylamine | 2-Hydroxybenzaldehyde | 192 | (DMSO) 4.20 (d, 2H, J = 5.8 Hz); 6.54 (d, 1H, J = 4.3 Hz); 6.65 (s, 1H); 6.74 (t, 1H, J = 7.4 Hz); 6.84 (d, 1H, J = 8.9 Hz); 7.06-7.13 (m, 2H); 7.26-7.29 (m, 1H); 7.75 (d, 1H, J = 5.8 Hz); 9.65 (s, 1H). |
| 4 | 2-[(2-Bromopyridin-4-ylamino)methyl]-4-fluorophenol | 2-Bromopyridin-4-ylamine | 5-Fluoro-2-hydroxybenzaldehyde | 153 | (DMSO) 4.36 (d, 2H, J = 4.8 Hz); 6.73 (t, 1H, J = 7.4 Hz); 6.81-6.84 (m, 2H); 7.04-7.08 (m, 2H); 7.14 (d, 1H, J = 7.4 Hz); 7.46-7.54 (m, 2H); 9.60 (s, 1H) |
| 5 | 2-[(2-Methoxypyridin-4-ylamino)methyl]phenol | 2-Methoxypyridin-4-ylamine | 2-Hydroxybenzaldehyde | Not determined | (DMSO) 3.70 (s, 3H); 4.17 (d, 2H, J = 5.8 Hz); 5.75 (s, 1H); 6.25 (d, 1H, J = 7.8 Hz); 6.73 (t, 1H, J = 7.5 Hz); 6.80-6.87 (m, 2H); 7.05 (t, 1H, J = 7.8 Hz); 7.11 (d, 1H, J = 8.8 Hz); 7.61 (d, 1H, J = 5.8 Hz), 9.59 (s, 1H), |
| 6 | 2-[(2-Bromo-6-methoxypyridin-4-ylamino)methyl]-4-fluorophenol | 2-Bromo-6-methoxypyridin-4-ylamine | 5-Fluoro-2-hydroxybenzaldehyde | 127 | (DMSO) 3.70 (s, 3H); 4.17-4.18 (d, 2H, J = 4 Hz); 5.80 (s, 1H); 6.46 (s, 1H); 6.79-6.83 (m, 1H); 6.88-6.93 (m, 2H); 7.21-7.24 (m, 1H); 9.71 (s, 1H). |
| 7 | 2-[(2-Bromo-6-methylpyridin-4-ylamino)methyl]phenol | salicylaldehyde | 2-bromo-6-methylpyridin-4-amine | 205 | (DMSO) 2.2 (s, 3H); 4.18-4.2 (d, 2H, J = 8 Hz); 6.4-6.41 (d, 1H, J = 4 Hz); 6.49 (s, 1H); 6.73-6.77 (q, 1H, 16 Hz); 6.82-6.84 (d, 1H, J = 8 Hz); 7.06-7.16 (m, 3H); 9.64 (s, 1H) |
| 8 | 2-[(2-Bromo-6-methylpyridin-4-ylamino)methyl]-4-fluorophenol | 5-Fluoro-2-hydroxybenzaldehyde | 2-bromo-6-methylpyridin-4-amine | 198 | (DMSO) 2.24 (s, 3H); 4.22-4.23 (d, 2H, J = 4 Hz); 6.44 (s, 1H); 6.52 (s, 1H); 6.83-6.86 (q, 1H, J = 12 Hz); 6.91-6.96 (m, 2H); 7.06-7.16 (m, 3H); 9.64 (s, 1H); 7.20-7.22 (d, 1H, J = 8 Hz), 9.8 (s, 1H). |

TABLE 1-continued

| Example # | IUPAC name | Starting material 1 | Starting material 2 | Melting point (° C.) | 1H NMR-400 MHz (s = singlet, d = doublet, t = triplet, m = multiplet, q = quartet, J = coupling constant in Hz) |
|---|---|---|---|---|---|
| 9 | 2-[(2-Bromo-6-methylpyridin-4-ylamino)methyl]-5-fluorophenol | 4-Fluoro-2-hydroxybenzaldehyde | 2-bromo-6-methylpyridin-4-amine | 200 | (DMSO) 2.2 (s, 3H); 4.15-4.16 (d, 2H, J = 4 Hz); 6.40 (s, 1H); 6.49 (s, 1H); 6.57-6.64 (m, 2H); 7.1-7.16 (m, 2H); 9.64 (s, 1H); 7.20-7.22 (d, 1H, J = 8 Hz), 10.2 (s, 1H) |
| 10 | 2-[(2-Bromo-6-methoxypyridin-4-ylamino)methyl]-6-fluorophenol | 2-bromo-6-methoxypyridine-4-amine | 2-hydroxy-3-fluorobenzaldehyde | 143 | (DMSO) 3.70 (s, 3H); 4.23-4.25 (d, 2 H, J = 8 Hz); 5.80 (s, 1H); 6.46 (s, 1H); 6.75-6.80 (m, 1H); 6.95-6.97(d, 1H, J = 8 Hz); 7.04-7.09 (tr, 1H); 7.22-7.24 (tr, 1H); 9.77 (s, 1H) |
| 11 | 2-[(2-Bromo-6-methoxypyridin-4-ylamino)methyl]-5-fluorophenol | 2-bromo-6-methoxypyridin-4-amine | 2-hydroxy-3-fluorobenzaldehyde | 192 | (DMSO) 3.70 (s, 3H); 4.13-4.14 (d, 2H, J = 4 Hz); 5.81 (s, 1H); 6.45 (s, 1H); 6.57-6.63 (m, 2H); 7:12-7.17 (m, 2H); 10.12 (s, 1H) |
| 12 | 2-[(2-Bromo-6-ethoxypyridin-4-ylamino)methyl]phenol | 2-bromo-6-ethoxypyridin-4-amine | Salycaldehyde | 156 | (DMSO) 1.20-1.24 (tr, 3H); 4.09-4.14 (q, 2H, J = 8 Hz, J' = 12 Hz); 4.16-4.18 (d, 2H, J = 8 Hz); 5.77 (s, 1H); 6.44 (s, 1H); 6.74-6.77 (tr, 1H); 6.82-6.84(d, 1H, J = 8 Hz); 7.05-7.18 (m, 3H); 9.63 (s, 1H) |
| 13 | 2-[(2-Bromo-6-methoxypyridin-4-ylamino)methyl]-5-methylphenol | 2-bromo-6-methoxypyridin-4-amine | 2-hydroxy-4-methylbenzaldehyde | 164 | (CDCl3) 2.31 (s, 3H); 3.88 (s, 1H); 4.30 (s, 2H); 4.50 (s, 1H); 5.91 (s, 1H); 6.44 (s, 1H); 6.66 (s, 1H); 6.73-6.75 (d, 1H, J = 7.7 Hz); 7.08-7.10 (d, 1H, J = 7.6 Hz) |
| 14 | 2-[(2-Bromo-6-methoxypyridin-4-ylamino)methyl]-6-methylphenol | 2-bromo-6-methoxypyridin-4-amine | 2-hydroxy-3-methylbenzaldehyde | 149 | (DMSO) 2.19 (s, 3H); 3.70 (s, 3H); 4.22-4.23 (d, 2H, J = 5.4 Hz); 5.80 (s, 1H); 6.45 (s, 1H); 6.70-6.73 (tr, 1H); 6.96-6.99 (m, 2H); 7.13-7.15 (m, 1H); 8.50 (s, 1H) |

Example 15

2-[(2-Trifluoromethylpyridin-4-ylamino)methyl]phenol

Synthesis According to Scheme 1, Method 1b 300 mg (1.65 mmol) of 4-chloro-2-(trifluoromethyl)pyridine are introduced into a microwave tube, 5 ml of dimethyl sulphoxide, 251 mg (1.65 mmol, 1 eq) of 1,8-diazabicyclo[5.4.0]undec-7-ene et 406 mg (3.3 mmol, 2 eq) of 2-aminomethylphenol are added thereto, and the mixture is heated in a microwave at 150° C. for 30 minutes. The reaction medium is diluted with 50 mL of ethyl acetate and then the mixture is washed with 50 mL of a saturated solution of ammonium chloride, followed by three times 50 mL of water. The organic phase is concentrated to dryness and the residue is purified by silica chromatography, elution being carried out with a mixture of heptane/ethyl acetate (7/3). 2-[(2-Trifluoromethylpyridin-4-ylamino)methyl]phenol is obtained in the form of a white solid.

1H NMR (DMSO) 4.27 (d, 2H, J=5.5 Hz); 6.69 (s, 1H); 6.76 (t, 1H, J=7.2 Hz); 6.84 (d, 1H, J=7.9 Hz); 6.97 (s, 1H); 7.09 (t, 1H, J=6.8 Hz); 7.15 (d, 1H, J=7.3 Hz); 7.47 (s, 1H); 8.12 (d, 1H, J=5.6 Hz); 9.68 (s, 1H).

All the NMR (nuclear magnetic resonance) spectra are in accordance with the proposed structures. The chemical shifts are expressed in parts per million. The internal reference is tetramethylsilane. The following abbreviations are used: CDCl3=deuterated chloroform, DMSO=deuterated dimethyl sulphoxide, CD3OD=deuterated methanol.

Example 16

Biological Tests

The compounds according to the invention show inhibitory properties on receptors of AR type. This AR receptor-inhibiting activity is measured in a transactivation test through the KdR (resting), KdA (active) and Kdapp (apparent) dissociation constants according to the method set out in J. Molecular Biology (1965), 12(1), 88-118, Monod J. of et al.

The expression "AR-type receptor inhibitor" means, according to the invention, any compound which has a Kdapp dissociation constant of less than or equal to 1 µM, and a KdR/Kda ratio≥10, in a transactivation test.

The preferred compounds of the present invention have a dissociation constant of less than or equal to 500 nM and advantageously less than or equal to 100 nM.

The transactivation test is carried out in the PALM (PC3 Androgen receptor Luciferase MMTV) cell line which is a stable transfectant containing the PMMTV-neo-Luc (reporter gene) and pSG5puro-AR plasmids.

In this study, the affinity of each product for the 2 receptor states (KdR and KdA) is determined, as is an apparent Kd (KdApp). This constant is a result of the 2 Kd, but also depends on the initial equilibrium of the receptor between the active state and the resting state ($L_0$) and on its expression level. It is determined by means of the following formula:

$$1/KdApp = (L0/(1+L0)) \times (1/KdR) + (1/(1+L0)) \times (1/KdA)$$

To determine these constants, "cross curves" of the test product against a reference agonist, methyltrienolone, are produced in 96-well plates. The test product is used at 10 concentrations and the reference agonist at 7 concentrations.

By way of illustration, a Kdapp of 20 nM is obtained for the compound (1), a Kdapp of 4 nM is obtained for the compound (2), a Kdapp of 20 nM is obtained for the compound (4), and a Kdapp of 50 nM is obtained for the compound (5).

The invention claimed is:

1. A compound of formula (I):

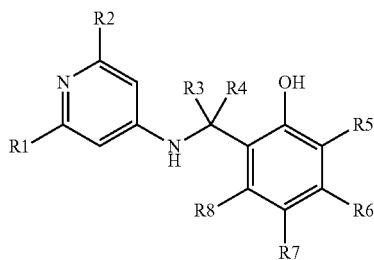

in which:
- $R_1$ represents a a hydrogen, a halogen, a methyl, an ethyl, an isopropyl, a trifluoromethyl, a nitrile, a nitro, a methoxy, an ethoxy, an isopropyl, a thiomethyl, a thioethyl, or a thioisopropyi;
- $R_2$ represents a a hydrogen atom, a halogen, a methyl, an ethyl, an isopropyl, a trifluoromethyl, a nitrile, a nitro, a methoxy, an ethoxy, an isopropyl, a thiomethyl, a thioethyl, or a thioisopropyl;
- $R_3$ and $R_4$ are identical or different and represent a hydrogen atom, a $C_{1-9}$ alkyl, a $C_{3-9}$ cycloalkyl, a $C_{1-6}$ fluoroalkyl, a —$(CH_2)_k$—$C_{3-9}$ cycloalkyl, a —$C_{2-6}$ alkyl-OH, a —$(CH_2)_p$—$C_{1-6}$ alkyloxy, a —$(CH_2)_k$—$C_{3-7}$ cycloalkyl, a —$(CH_2)_k$—$C_{1-6}$ fluoroalkyl or a —$(CH_2)_r$—O—$C_{1-6}$ fluoroalkyl group,
- optionally, the $R_3$ and $R_4$ groups together with the carbon atom form a $C_{3-9}$ cycloalkyl group or a heterocycle;
- $R_6$, $R_6$, $R_7$ and $R_8$ are identical or different and represent a hydrogen atom, a $C_{1-6}$ alkyl, a $C_{3-7}$ cycloalkyl, a $C_{1-6}$ alkyloxy, a —$S(O)_g$—$C_{1-6}$ alkyl, a $C_{1-6}$ fluoroalkyl, a $C_{1-6}$ fluoroalkyloxy, a —$(CH_2)_j$—$C_{3-9}$ cycloalkyl, a —$(CH_2)_j$—$C_{3-9}$ cycloalkyl, a —$C_{1-6}$ alkyl-OH, a —$(CH_2)_j$—$C_{1-6}$ alkyloxy, a —$(CH_2)_j$—$C_{1-6}$ fluoroalkyl, a —$(CH_2)_s$—O—$C_{1-6}$ fluoroalkyl, $COR_e$, CN, a $NR_{11}R_{12}$ group, a halogen, or a phenyl;

and also a pharmaceutically acceptable salt, solvate or hydrate thereof and the conformer or rotamer thereof.

2. The compound as defined in claim 1, wherein:
- $R_2$ represents a hydrogen atom, a halogen, a methoxy, an ethoxy, a thiomethyl, a thioethyl or a trifluoromethyl group.

3. The compound of claim 1, wherein $R_3$ and $R_4$ groups together with the carbon atom form a heterocycle selected from the group consisting of a tetrahydrofuran, a tetrahydropyran, a tetrahydrothiopyran, a tetrahydro-1-oxythiopyran, and a tetrahydro-1,1-dioxythiopyran.

4. A method of inhibiting androgen receptor activity, wherein the method comprises contacting an androgen receptor with a compound of claim 1, a pharmaceutically acceptable salt thereof, a solvate thereof, a hydrate thereof, a conformer thereof or a rotamer thereof; and wherein the compound of claim 1 has a Kdapp dissociation constant of less than or equal to 500 nM.

5. The method of claim 4, wherein the androgen receptor is expressed in a cell.

6. The method of claim 4, wherein the compound has a Kdapp dissociation constant of less than or equal to 100 nM.

7. A composition comprising the compound of claim 1, a pharmaceutically acceptable salt thereof, a solvate thereof, a hydrate thereof, a conformer thereof or a rotamer thereof.

8. The composition of claim 7, wherein the composition is a pharmaceutical composition.

9. The composition of claim 7, wherein the composition is a cosmetic composition.

10. The method of claim 4, wherein the compound is selected from the group consisting of:
- 2-[(2-bromo-6-methoxypyridin4-ylamino)methyl]phenol;
- 2-[(2-chloropyridin-4-ylamino)methyl]phenol;
- 2-[(2-bromopyridin4-ylamino)methyl]phenol;
- 2-[(2-bromopyridin-4-ylamino)methyl]-4-fluorophenol;
- 2-[(2-methoxypyridin-4-ylamino)methyl]phenol;
- 2-[(2-bromo-6-methoxypyridin-4-ylamino)methyl]-4-fluorophenol;
- 2-[(2-bromo-6-methyipyhdin-4-ylamino)methyl]phenol;
- 2-[(2-bromo-6-methylpyridin-4-ylamino)methyl]-4-fluorophenol;
- 2-[(2-bromo-6-methylpyridin-4-ylamino)methyl]-5-fluorophenol;
- 2-[(2-bromo-6-methoxypyridin-4-ylamino)methyl]-6-fluorophenol;
- 2-[(2-bromo-6-methoxypyridin-4-ylamino)methyl]-5-fluorophenol;
- 2-[(2-bromo-6-ethoxypyridin4-ylamino)methyl]phenol;
- 2-[(2-promo-6-methoxypyridin-4-ylamino)methyl]-5-methylphenol;
- 2-[(2-promo-6-methoxypyridin-4-ylamino)methyl]-6-methylphenol; and
- 2-[(2-trifluoromethylpyridin-4-ylamino)methyl]phenol.

* * * * *